Figure 1:
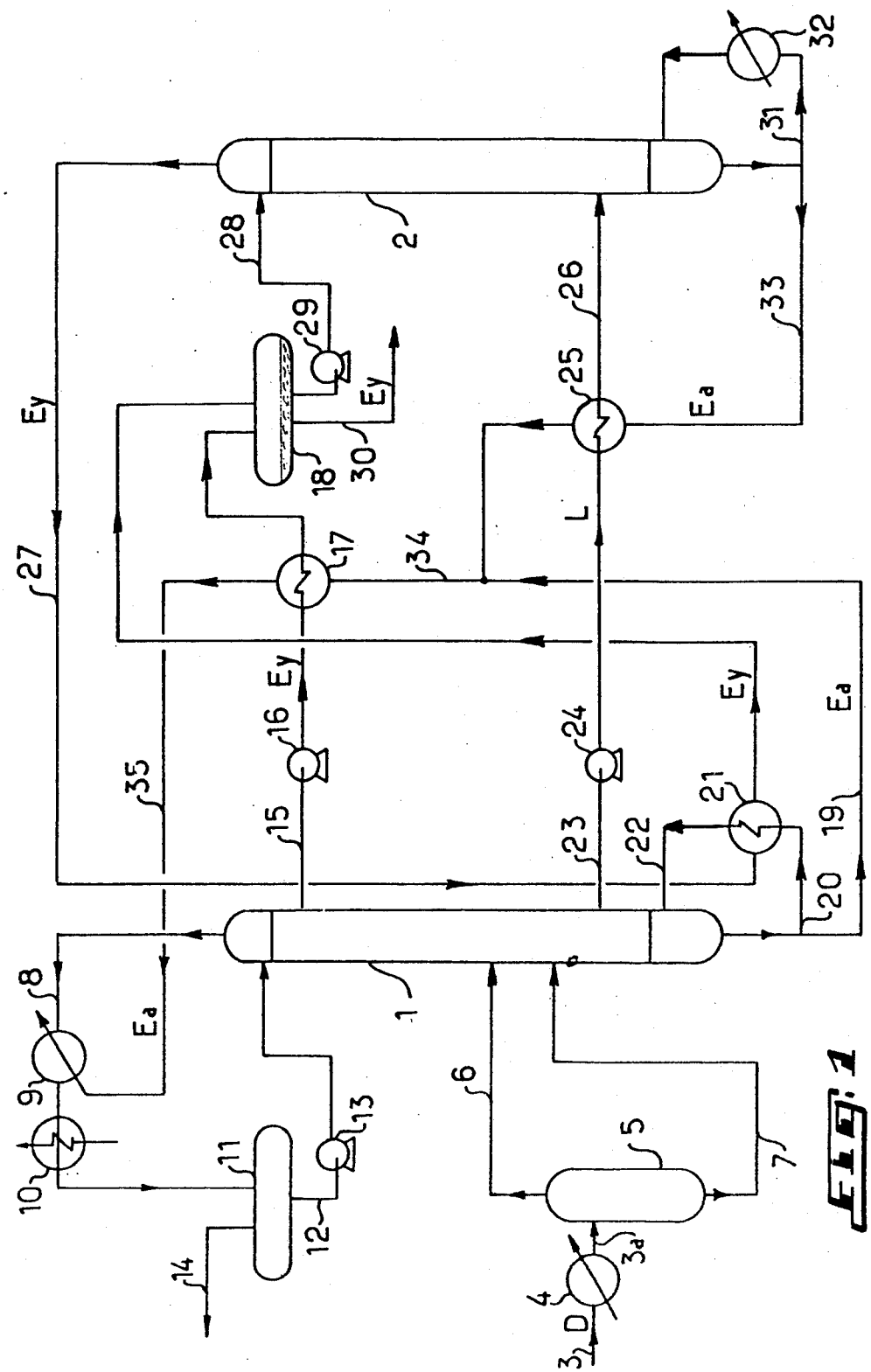

United States Patent [19]
Kaiser et al.

[11] Patent Number: 4,460,396
[45] Date of Patent: Jul. 17, 1984

[54] METHOD FOR PRODUCING PURIFIED ETHYLENE THROUGH THERMO-COUPLED DISTILLATION AND ETHYLENE-PRODUCING APPARATUS USING THE SAID METHOD

[75] Inventors: Victor Kaiser, Maisons Laffitte; Gérard Heck, Louveciennes; Philippe Lepetit, Marly-le-Roi, all of France

[73] Assignee: Compagnie Francaise d'Etudes et de Construction "Technip", Paris, France

[21] Appl. No.: 398,310

[22] Filed: Jul. 15, 1982

[30] Foreign Application Priority Data
Sep. 2, 1981 [FR] France .............................. 81 16707
Jan. 22, 1982 [FR] France .............................. 82 01018

[51] Int. Cl.$^3$ .............................................. F25J 3/02
[52] U.S. Cl. ............................................ 62/28; 62/30; 62/31; 62/34

[58] Field of Search ...................... 203/24, 26, 57, 58, 203/59, 62, 71, 73, 75, 77, 78, 80, 82, 84, 91, 93, 94, 98, DIG. 4; 208/325–327, 330–333, 354, 355, 357, 358; 585/810, 860, 862, 864, 865, 901; 196/100, 105, 106, 111; 62/26, 27, 30, 28, 29, 31, 34, 33, 24

[56] References Cited
U.S. PATENT DOCUMENTS
3,058,893 10/1962 Cahn et al. ......................... 203/82

Primary Examiner—Frank Sever
Attorney, Agent, or Firm—Kenyon & Kenyon

[57] ABSTRACT

The present invention relates to a method and an apparatus for producing ethylene. This apparatus comprises essentially a phase separator connected to an ethylene fractionating unit. The fractionating unit comprises a first or lower-pressure fractionating column and a second or higher-pressure fractionating column, the second column being fed with an intermediate liquid fraction from the first column and having its head connected to the heating circuit of the reboiling system associated with the first column to at least partially condense the head fraction of the second column. Thus, the invention allows high-purity ethylene to be produced with minimum energy consumption.

24 Claims, 2 Drawing Figures

METHOD FOR PRODUCING PURIFIED ETHYLENE THROUGH THERMO-COUPLED DISTILLATION AND ETHYLENE-PRODUCING APPARATUS USING THE SAID METHOD

The present invention has essentially for a subject matter an improved method for producing purified ethylene from a condensate of hydrocarbons enriched with hydrocarbons with two carbon atoms ($C_2$).

It is also directed to a purified ethylene-producing apparatus or plant for carrying out the said method.

There are already known ethylene producing apparatuses using the vapour cracking method. Such apparatus comprise among other things a de-ethanizing column and an ethylene superfractionating section which allows high-purity ethylene to be produced from a condensate of hydrocarbons enriched with hydrocarbons having two carbon atoms, and which the acetylene has advantageously been eliminated by an appropriate method such as for example selective hydrogenation, solvent extraction or the like.

Such units comprise a certain number of devices such as for example various compressors which require a supply of considerable energy for their driving.

The energy consumption of those various devices of course depends on many factors, such as the capacity of the producing unit, the method adopted, the environmental conditions, etc. However, the present ethylene-producing units generally remain considerable energy consumers.

Thus, one such device allows cold or negative calories to be supplied in a temperature range comprised between $-45°$ C. and $+45°$ C., which are necessary particularly for refrigerating the fluids in the de-ethanizing and ethylene superfractionating sections of the apparatus. Indeed, a study of the energy consumptions in a vapour cracking apparatus shows that from about 30 to 40% of the power consumed by this device corresponds to the consumption of cold by the ethylene superfractionating section.

The purpose of the present invention, therefore, is particularly to remedy this drawback by providing an improved method and an improved apparatus for producing purified ethylene, which allow a considerable reduction of the energy consumption of the refrigerating device, or otherwise stated, the consumption of negative calories by the ethylene superfractionating section.

To this end, the invention has for a subject matter an ethylene-producing method, of the type consisting in cooling a condensate of hydrocarbons enriched with hydrocarbons with two carbon atoms ($C_2$) to condensate at least part thereof, in sending the said hydrocarbons to a phase separator, and in sending the said separated phases to an ethylene recovery unit, the said method being characterized in that, with a view to substantially reducing the energy consumption of the ethylene recovery unit, the said separated phases are sent to a first or "lower-pressure" fractionating column, a second or "higher-pressure" fractionating column is fed with at least a portion of a liquid fraction intermediate between the head fraction and the bottom fraction of the said first fractionating column, and the head fraction of the said second fractionating column is condensed at least partially through heat exchange with at least a portion of the reflux fluid of the said first column flowing in the reboiling system associated with the said first fractionating column.

According to another characterizing feature of the method of the invention, the light products, or otherwise stated, the products whose boiling point is lower than that of ethylene, are substantially entirely eliminated in the first or lower-pressure fractionating column.

Moreover, in order to additionally reduce energy consumption, a heat exchange is effected between the bottom products of the first fractionating column and/or the second fractionating column, and the head products of the first fractionating column comprising ethylene substantially of the desired purity, and/or the hydrogen cut fed to the second fractionating column.

Advantageously, an additional heat exchange is effected between the bottom products of at least one of the first and second fractionating columns, and the light impurities or the products whose boiling point is lower than the boiling point of ethylene, extracted from the first or lower-pressure fractionating column.

Thus, by judiciously selecting the operating pressures of the first and second columns, and of the feed rate of the second column, there is obtained a thermal equilibrium of the two ethylene fractionating columns which are thus integrated to provide a thermocoupled or thermally coupled distillation, and such temperatures that the cold available in the first fractionating column will be recovered at the reboiling system of the first fractionating column to be transferred particularly to the ethylene produced, and there will also be recovered, at the complementary heat exchangers, the cold available in the various fractions drawn from the first column to be returned to the ethane recycling vapourizer by conventional and widely-known methods.

More specifically, in an apparatus according to the present invention, the pressure above atmospheric and the operating temperature of the lower pressure fractionating column bottom are comprised respectively between about $15 \times 10^5$ and $25 \times 10^5$ Pa and between about $-15°$ C. and $+3°$ C., whereas the pressure above atmospheric and the operating temperature of the second or higher pressure fractionating column head are comprised respectively between about $28 \times 10^5$ and $45 \times 10^5$ Pa and between about $-13°$ C. and $+5°$ C.

Further, the feed rate of the second fractionating column is comprised between about 25% and 75% of the total feed rate of the condensate enriched with hydrocarbons having two carbon atoms in the fractionating section, and preferably comprised between about 40% and 50%, whereas the ethylene content of the feed to the second or higher-pressure column is comprised between about 85% and 30% by weight, and advantageously between about 45% and 35% by weight.

According to a second form of embodiment of the method of the invention, particularly for treating a condensate of hydrocarbons with for example two carbon atoms ($C_2$), obtained from naphtha and/or gas-oil cracking, the intermediate liquid fraction feed to the second fractionating column is drawn off at the first bottom tray of the first fractionating column.

Indeed, since the amount of ethane associated with the ethylene in the hydrocarbon condensate is sufficiently small, it is no longer necessary to produce pure ethane at the bottom of the first fractionating column, the totality of the ethane then being produced by the second fractionating column.

Preferably, the said bottom fraction is drawn from the first fractionating column only upon starting the apparatus and in order to reduce the concentration of products with a higher boiling point than those of ethylene and ethane in the bottom of the first fractionating column.

Under such conditions, there is a mixture of ethylene and ethane at the bottom of the first fractionating column therefore the bottom temperature of this column is lower. Thus the operating above-atmospheric pressure of the second fractionating column is lower, as also its head temperature.

Consequently, the separation of ethylene and ethane in the second fractionating column is easier, thus allowing the investment expenditure connected with this second fractionating column to be reduced. It should be pointed out here that in an apparatus according to this second form of embodiment, the effective pressure and the operating temperature of the bottom of the first or lower-pressure fractionating column are comprised between about $15 \times 10^5$ Pa and $25 \times 10^5$ Pa and between about $-30°$ C. and $+3°$ C., respectively, whereas the effective pressure and the operating temperature at the top of the second or higher-pressure fractionating column are comprised between about $20 \times 10^5$ Pa and $45 \times 10^5$ Pa and between about $-28°$ C. and $+5°$ C., respectively.

Further, the second fractionating column feed rate is comprised between about 25% and 75% of the total feed rate of the condensate enriched with hydrocarbons with two carbon atoms in the fractionating section, and preferably comprised between about 40% and 50%, whereas the ethylene content of the feed to the second or higher-pressure column is comprised between about 85% and 30% by weight, advantageously between about 70% and 35% by weight.

Figure 2:
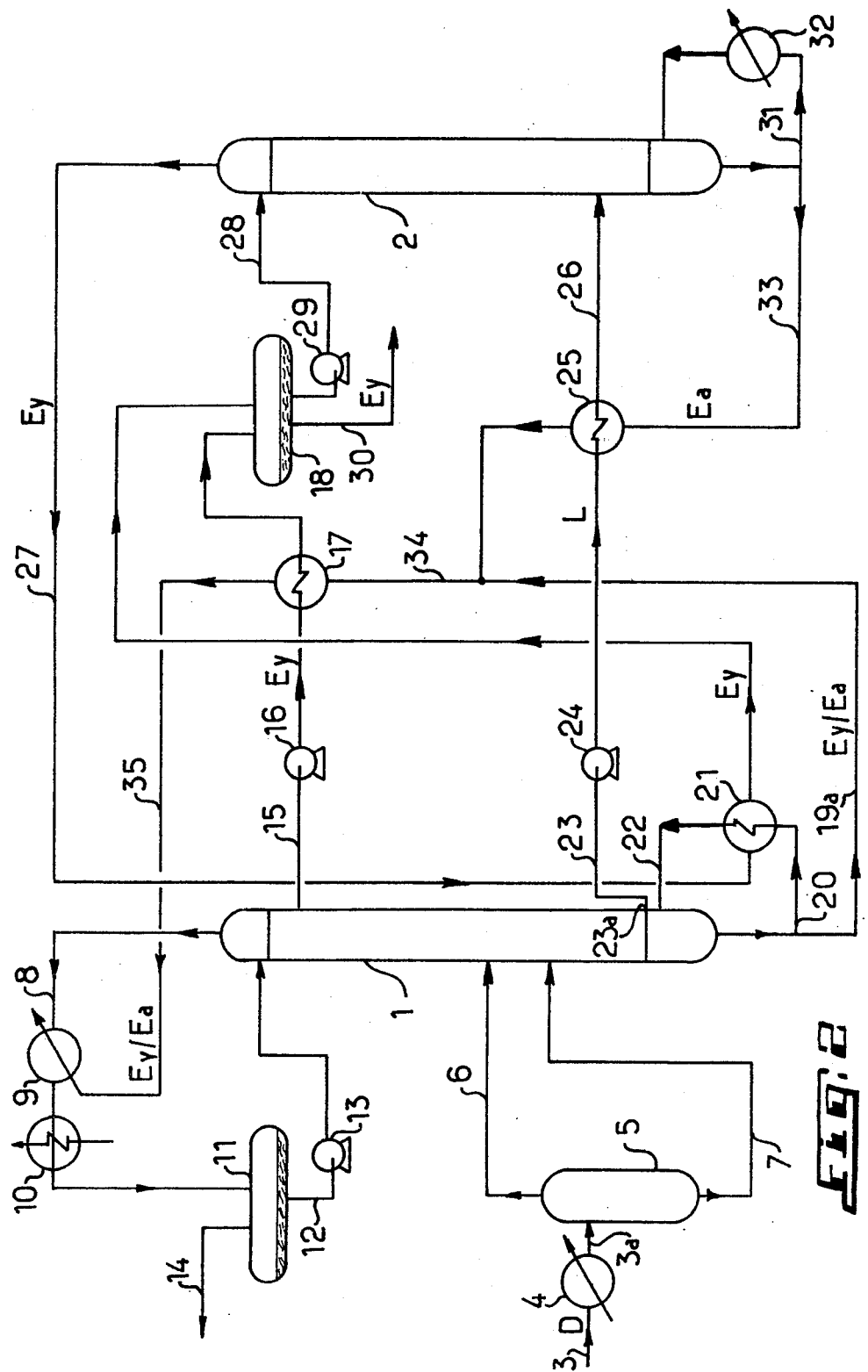

Preferred values of temperature, feed rate and ethylene content of the feed to the second column will be given in the detailed description which follows and in which there will be described other characterizing features and advantages of the invention with reference to the appended drawings given solely by way of example and illustrating two forms of embodiment of the method and the apparatus according to the invention, wherein:

FIG. 1 is a diagrammatic view illustrating an ethylene-producing unit according to a first form of embodiment of the method of the invention, and FIG. 2 is a view similar to that of FIG. 1, illustrating an ethylene-producing unit according to a second form of embodiment of the method of the invention.

According to an example of a first form of embodiment, and referring to FIG. 1, a purified ethylene-producing apparatus or plant of the type concerned comprises essentially a first or lower-pressure fractionating column 1 and a second or higher-pressure fractionating column 2, each of which processes a portion of a hydrocarbon condensate containing essentially hydrocarbons having two carbon atoms ($C_2$) and impurities whose boiling points are lower than that of ethylene or higher than that of ethane. The fractionating columns 1 and 2 constitute the ethylene superfractionating section in an ethylene-producing apparatus.

Hereafter will be described in detail the various elements of this superfractionating section together with its operation.

The condensate of hydrocarbons enriched with hydrocarbons having two carbon atoms may be for example the head fraction of a de-ethanizing column (not shown) which may possibly be processed to eliminate or convert the acetylene by a selective hydrogenation method or a solvent-extracting operation or the like.

The hydrocarbon condensate thus obtained contains mainly ethane and ethylene accompanied by light and/or heavy impurities whose boiling points are respectively lower and higher than those of ethylene or of ethane, such as for example hydrogen, carbon monoxide, methane, propylene. For example, the said impurities are present at concentrations of the order of 0.01% by volume for hydrogen, 0.005% by volume for carbon monoxide, 0.5% by volume for methane and 0.3% by volume for propylene, the rest of the mixture being constituted by ethane and ethylene.

This hydrocarbon mixture D is admitted through duct 3 to a heat exchanger 4 where it receives the cold from a refrigerating fluid which vaporizes, such as for example propylene or propane. The hydrocarbon mixture D is available at a pressure above atmospheric comprised for example between about $17 \times 10^5$ Pa and $28 \times 10^5$ Pa, and for example at $25 \times 10^5$ Pa.

In the said exchanger the hydrocarbon mixture D condenses partially so that the condensed liquid phase represents from 25 to 75% of the total weight of the mixture D for example 40% by weight. The combined phase leaving the condensor 4 through the duct 3a is fed to a separator 5.

The separated liquid and gaseous phases are sent respectively through the ducts 7, 6 to the first or lower-pressure fractionating column 1 whose bottom operating pressure above atmospheric is for example $17 \times 10^5$ Pa.

This first fractionating column 1 allows ethylene Ey to be produced with a high degree of purity and ethane Ea meeting the required specification can be obtained at its bottom. The hydrocarbon gases collected at the head of column 1 are recycled to the latter by passing through a circuit comprising a duct 8, a heat exchanger 9 (described later), another heat exchanger 10 in which the refrigerating fluid is an external fluid such as propylene, ammonia or the like, a phase separator or receiving flask or like vessel 11, and a duct 12 comprising a recycling pump 13. The gaseous phase constituted by the light hydrocarbon vapours and ethylene, contained in the separating tank 11, is eliminated through the duct 14 and may advantageously be reprocessed by known methods. In fact, the head section of column 1 located above the high-purity ethylene withdrawing duct 15 allows the light hydrocarbons to be concentrated and removed from the separating flask 11.

The high purity ethylene Ey is withdrawn through the duct 15 and sent by a pump 16 through a heat exchanger 17 into an ethylene separating flask or like vessel or tank 18.

Advantageously, the cold from the ethylene produced by the first fractionating column 1 is transferred to the ethane Ea produced at the bottom of the fractionating columns 1 and 2.

The ethane produced at the bottom of the first fractionating column is withdrawn through the duct 19 and the aforementioned heat exchanger 17. Moreover, the fractionating column 1 comprises a reboiling system constituted by a duct 20 allowing part of the liquid products to be withdrawn from the bottom of the said first column into a heat exchanger 21 constituting the reboiler of the first fractionating column and the hydrocarbons to be recycled to column 1 through the duct 22.

According to the first form of embodiment of the invention, a duct 23 allows lateral withdrawal, from a predetermined intermediate region of column 1, of a liquid hydrocarbon mixture L which is sent by the pump 24 through heat exchanger 25 as a feed liquid for the second or higher-pressure fractionating column 2 through the conduit 26.

It will be noted that, according to the invention, it is necessary to cause the feed to the second fractionating column 2 to pass through the first or lower-pressure column 1 to feed the latter with a hydrocarbon mixture L which no longer contains light impurities such as hydrogen, carbon monoxide or methane, which are eliminated through conduit 14 as described previously.

One important characterizing feature of the invention is that the heating circuit of the reboiler 21 of the reboiling system associated with the first fractionating column 1 is constituted by the duct 27 connected to the head of the second fractionating column 2 to feed the head product of the said column 2 constituted by ethylene Ey having the required degree of purity to the reboiler 21 to be preferably completely condensed in the latter.

For example, the Ey gases proceeding from the head of column 2 are at a temperature of about $-6°$ C. and give up heat to the liquid of the reboiling circuit 20 which is at a temperature of the order of $-10°$ C. Thus, the head gases of the column 2 are completely condensed at a temperature of about $-6°$ C. before being admitted to the ethylene-receiver tank 18. The operation and feed of the second or higher pressure fractionating column 2 are so selected that the product obtained at the head of this column be high purity ethylene meeting the same specifications as the high purity ethylene withdrawn into the duct 15 of the first column 1 and sent to the same separating tank 18 by the pump 16, and moreover, so as to obtain a preferably substantially total condensation of the said head products in the reboiler 21 associated with the first column 1.

A portion of the liquid phase contained in the separating flask 18 is sent as a reflux flow for the fractionating column 2 by a pump 21 through a duct 28.

Furthermore, the separating tank 18 comprises a duct 30 through which the high purity ethylene Ey produced in both fractionating columns 1 and 2 is withdrawn.

The second or higher-pressure column 2 comprises a reboiling system constituted by a duct 31 and a reboiler 32 for recovering heat from a heat fluid such as for example the condensation heat of a certain amount of refrigerating fluid. The ethane Ea produced at the bottom of the higher-pressure column 2 is recovered through the duct 33. This bottom product recovers in the heat exchanger 25 the excess cold from the feed liquid L of the higher pressure column 2 and is then mixed in the duct 34 with the ethane product at the bottom of the lower pressure column and withdrawn from the duct 19. This mixture passes through exchanger 17 where it recovers the available excess cold from the high purity ethylene produced by column 1, which ethylene may be partially vaporized in the heat exchanger 17. The total production of the ethane is then available in the duct 35 and may be recycled as a partial charge to the ethylene unit.

This recovery of cold obtained in the exchangers 25 and 17 allows an over-cooling of the bottom products Ea of the columns 1 and 2 especially when the temperature of the ethane is lowered to values of for example $-30°$ C. This recovery allows the energy consumption in the ethylene superfractionating section to be lowered quite interestingly and significantly, particularly by returning this cold in the condensor 9 to the head gases of the first column 1.

There is therefore obtained according to the invention an ethylene fractionating method and apparatus which allow the cold available in the fractionating column to be recovered so as to be transferred by refluxing to another fractionating column, by judiciously and appropriately selecting the operating pressures of the two columns and the feed rate to the higher pressure column which is supplied with a liquid containing no light impurities.

It is thus possible to completely condensate the head products of the higher pressure column without however reaching excessive operating pressures and to thus supply the necessary heat to the reboiling systems of the first or lower pressure column. All those measures together result in a quite reduced consumption of cold at the condensor 10 and therefore a reduction of the power of the external refrigerating device. Moreover, it is not necessary to provide a condenser for the head fraction of the second column consuming the cold supplied by an external refrigerating device.

By way of example, Table 1 comparatively shows various energies consumed by the elements of a conventional single-column superfractionating section and by a superfractionating section according to the invention.

In this example, the condensate D has an ethylene content of 60% by weight and is supplied at a rate of 2,246 kmoles/h. The flow rate of the feed liquid to the second column is 1,023 kmoles/h (45.54% D) with an ethylene content of 35.25% by weight, the flow rate of the collected ethylene is 1,326 kmoles/h. The operating temperatures and pressures of the columns are equal to those indicated previously.

TABLE 1

| Comparative energy values for obtaining 1 ton of ethylene of required purity | | |
|---|---|---|
| | System according to the invention (FIG. 1) | Conventional single-column system |
| Thermal load Condenser 10 | 0.87 GJ | 1.72 GJ |
| Equivalent refrigerating power of Condenser 10 | 150 kwhrs | 290 kwhrs |
| Refrigerating power of the whole system (pumping included) | 155 kwhrs | 200 kwhrs |
| Refrigerating compressor suction volume | 1360 m$^3$ | 2040 m$^3$ |

The data in the above table strikingly show the reduction in equivalent refrigerating power of the condenser 10 and of the whole of the superfractionating section with respect to the refrigerating power of a conventional apparatus. Moreover, the refrigerating compressor suction volume being smaller, it is easier to find the standard material for equipping the high capacity units constructed according to the invention.

According to a second form of embodiment of the method of the invention, carried out in the apparatus shown in FIG. 2, the processed condensate D of hydrocarbons with two carbon atoms (C$_2$) is obtained for example from naphtha and/or gas-oil cracking and comprises a small amount of ethane with respect to ethylene. The weight ethylene content of the said condensate is advantageously of the order of about 82%. The condensate may also contain light and/or heavy impurities having lower and higher boiling points, respectively, than those of ethylene or of ethane, such as for example hydrogen, carbon monoxide, methane, propylene.

This is the mixture D of hydrocarbons that is fed to the first fractionating column 1 of the ethylene producing unit of FIG. 2 after partial condensation of the said mixture in an apparatus comprising mainly a condenser 4 and a phase separator 5 identical to those of the apparatus of FIG. 1.

The apparatus illustrated in FIG. 2 differs from that of FIG. 1 only by the position of the point of withdrawal 23a of the hydrocarbon mixture L no longer containing light impurities such as hydrogen, carbon monoxide or methane, and by the reboiling system of the first column 1.

Indeed, since the amount of ethane associated with ethylene in the hydrocarbon condensate D is sufficiently small, the totality of the reboil flow from the fractionating column 1 is recycled, no fluid being generally withdrawn through the duct 19a during normal operation of the apparatus, and the point of withdrawal 23a of the hydrocarbon mixture L supplied to the column 2 is located in the region of the first bottom tray of the fractionating column 1. There is thus an ethylene-ethane mixture in the bottom of column 1, resulting in a lower bottom temperature in column 1 and therefore a lower head temperature in column 2, as also the pressure in this column.

For example, the Ey gases proceeding from the head of the column 2 are at a temperature of about −23° C., they give up heat to the liquid in the reboiling circuit 20 which is at a temperature of the order of −26° C. Thus, the gases at the head of column 2 are condensed totally at a temperature of about −23° C. before being admitted to the ethylene receiver tank 18, the operating above-atmospheric pressure at the bottom of the first column 1 being for example equal to about $17 \times 10^5$ Pa.

In the apparatus of FIG. 1, the operation and the dimensions of the second or higher-pressure fractionating column 2 are so selected that the product obtained at the head of this column is high-purity ethylene complying with the same specifications as the high-purity ethylene withdrawn into the duct 15 of the first column 1 and sent to the same separating tank 18 by the pump 16 and also to ensure a preferably substantially total condensation of these head products in the reboiler 21 associated with the first column 1.

It is thus possible, in this form of embodiment of the method and apparatus according to the invention, to produce the totality of the ethane in the bottom of the second fractionating column and to lower the operating temperature and pressure of the second fractionating column 2, thus allowing easier separation of ethylene and ethane and therefore a reduction of investment expenditure in connection with this column.

However, it may be necessary to withdraw a portion of the bottom product of the fractionating column 1 through the duct 19a, especially during the starting of the apparatus, and intermittently during the normal operation of the apparatus to reduce the concentration of product with a higher boiling point than those of ethylene and ethane in the bottom of the first column.

Table 2 below shows the important reduction of energy consumption obtained in the ethylene-producing unit illustrated in FIG. 2 as compared to a conventional single-column ethylene producing unit.

In this example, the ethylene content of the condensate D is 82% by weight, the condensate feed rate is 2,622 kmoles/h. The flow rate of the feed liquid L to the second column is 1,309 kmoles/h (50% D) with an ethylene content of 64.8% by weight, the flow rate of the collected ethylene is 2,159 kmoles/h. The operating temperatures and pressures of the columns are equal to those mentioned earlier.

TABLE 2

| Comparative energy values for obtaining 1 ton of ethylene of required purity | | |
|---|---|---|
| | System of the invention according to FIG. 2 | Conventional single-column system |
| Thermal load of Condenser 10 | 0.84 GJ | 1.52 GJ |
| Equivalent refrigerating power of Condenser 10 | 145 kwhrs | 255 kwhrs |
| Refrigerating power of the whole system (pumping included) | 123 kwhrs | 170 kwhrs |
| Refrigerating compressor suction volume | 870 m$^3$ | 2,040 m$^3$ |

Moreover, since the amount of ethane associated with ethylene in the condensate D enriched with hydrocarbon with two carbon atoms ($C_2$) is relatively small, the energy consumption and the dimensions of the second fractionating column 2 of the apparatus of FIG. 2 are smaller than those of the apparatus illustrated in FIG. 1.

The method of the invention therefore allows a notable and important reduction in the energy consumption of an ethylene superfractionating unit, but offers also the following advantages:

the impurities having lower boiling points than ethylene, such as carbon monoxide, methane and hydrogen, are completely eliminated in the first column, thus substantially reducing the operating costs of the second fractionating column;

it is also very easy to modify an existing unit, or to perform its unspouting to obtain a unit according to the present invention. Indeed, it is sufficient to re-utilize the first column without modification and to integrate a second column complying with the second fractionating column 2. The refrigerating power of such a modified apparatus is practically not increased, whereas the production of ethylene increases by about 45%;

at low capacity, for example in the starting phase, the first column 1 alone ensures production of high-purity ethylene. The second column is fed as the production of ethylene increases until the nominal capacity of the apparatus is reached.

It will also be noted that, depending on the flow rate of the condensate D, its ethylene content, the pressures above atmospheric and the operating temperatures of the fractionating columns 1, 2, it is possible to do away with at least one of the heat exchangers 25, 17, 19 without however departing from the scope of the invention.

What is claimed is:

1. A method for producing purified ethylene, of the type consisting in cooling a condensate of hydrocarbons enriched with hydrocarbons having two carbon atoms ($C_2$) to condense at least a portion thereof, in sending the said hydrocarbons to a phase separator, and in sending the said separated phases to an ethylene-recovery unit, characterized in that it consists in sending the said separated phases to a first or lower-pressure fractionating column, in feeding a second or higher-pressure fractionating column with at least a portion L of a liquid fraction intermediate between the head fraction and the bottom fraction of the said first fractionating column, and in condensating at least partially the head fraction of the second fractionating column through heat exchange with at least a portion of the reflux fluid of the said first column flowing in the reboiling system associated with the said first column.

2. A method according to claim 1, characterized in that the light products or impurities whose boiling points are lower than those of ethylene are eliminated from the head gases of the aforesaid first fractionating column.

3. A method according to claim 1, characterized by a heat exchange between the bottom products Ea of the said first fractionating column and/or the said second fractionating column and the head product Ey of the said first fractionating column and/or a liquid fraction feed L to the second fractionating column.

4. A method according to claim 1, characterized by a heat exchange between the bottom products Ea of at least one of the said first and second fractionating columns and the head gases of the said first fractionating column.

5. A method according to claim 1, characterized in that the pressure above atmospheric and the bottom operating temperature of the said first fractionating column are comprised between about $15 \times 10^5$ Pa and $25 \times 10^5$ Pa and between about $-15°$ C. and $+3°$ C., respectively, and in that the pressure above atmospheric and the operating temperature at the head of the said second fractionating column are comprised between about $28 \times 10^5$ and $45 \times 10^5$ Pa and between about $-13°$ C. and $+5°$ C., respectively.

6. A method according to claim 1, characterized in that the flow rate of the hydrocarbon liquid fraction feed L to the said second fractionating column is equal to about 25% to 75% of the flow rate of the hydrocarbon condensate D fed to the said first fractionating column, the weight concentration of ethylene in the said liquid fraction L being comprised between about 85% and 35%.

7. A method according to claim 6, characterized in that the flow rate of the hydrocarbon liquid fraction feed L to the second fractionating column is about 40% to 50% and the weight concentration of ethylene in the said liquid fraction is comprised between about 35% and 45%.

8. A method according to claim 1, consisting in processing a hydrocarbon condensate enriched with hydrocarbons with two atoms of carbon obtained for example from naphtha and/or gas oil cracking, characterized in that the said intermediate liquid fraction feed L to the second fractionating column 2 is withdrawn in the region of the first bottom tray of the said first fractionating column 1.

9. A method according to claim 8, characterized in that the flow rate of the hydrocarbon liquid fraction L admitted to the said second fractionating column is equal to about 25% to 75% of the flow rate of the hydrocarbon condensate D admitted to the said first fractionating column, advantageously about 40% to 50%, and the weight concentration of ethylene in the said liquid fraction L is comprised between about 85 to 30%, advantageously between 70% and 35%.

10. A method according to claim 8, characterized in that the pressure above atmospheric and the operating temperature at the bottom of the said first fractionating column are comprised between about $15 \times 10^5$ Pa and $25 \times 10^5$ Pa, respectively, and between about $-30°$ C. and $+3°$ C., respectively, and in that the pressure above atmospheric and the operating temperature at the head of the said second fractionating column are comprised between about $20 \times 10^5$ Pa and $45 \times 10^5$ Pa and between about $-28°$ C. and $+5°$ C., respectively.

11. A method according to claim 8, characterized in that at least a portion of the bottom fraction of the first fractionating column is withdrawn only during the phase of starting of the apparatus and intermittently, during the normal operation of the apparatus to reduce the concentration of products with higher boiling points than those of ethylene and ethane in the bottom of the said first fractionating column.

12. A method according to claim 8 characterized in that the light products or impurities whose boiling points are lower than those of ethylene are eliminated from the head gases of the aforesaid first fractionating column.

13. A method according to claim 8, characterized by a heat exchange between the bottom products Ea of the said first fractionating column and/or the said second fractionating column and the head product Ey of the said first fractionating column and/or a liquid fraction feed L to the second fractionating column.

14. A method according to claim 8, characterized by a heat exchange between the bottom products Ea of at least one of the said first and second fractionating columns and the head gases of the said first fractionating column.

15. A method according to claim 1 carried out in an apparatus comprising at least one separator connected to an ethylene fractionating unit, characterized in that the said fractionating unit comprises a first or lower-pressure fractionating column with an associated reboiling system constituted by a heating fluid circuit and a reflux fluid circuit of the said fractionating column, and a second or higher-pressure fractionating column, the head of the said second fractionating column being connected to the said heating circuit of the reboiling system associated with the first fractionating column, and the heat duct of the said second column being connected to a withdrawing duct from the said first fractionating column, the said withdrawing duct being located in an intermediate region of the said first fractionating column.

16. A method according to claim 15, wherein said apparatus is characterized by a first heat exchanger, one of the circuits of which is connected to the feed duct to the second fractionating column, whereas the other circuit is connected either to the bottom of the said second fractionating column or to the bottom of the said first fractionating column.

17. A method according to claim 16, wherein said apparatus is characterized by a second heat exchanger, one of the circuits of which is connected to the head of the first fractionating column, whereas the other circuit is connected to the bottom of the said first fractionating column and/or to the bottom of the second fractionating column.

18. A method according to claim 17, wherein said apparatus is characterized by a third heat exchanger, one of the circuits of which is connected to the gas withdrawing duct from the head of the said first fractionating column, whereas the other circuit is connected to the bottom of the first fractionating column and/or to the bottom of the second fractionating column and, preferably, downstream of the first and second heat exchanger, if any.

19. A method according to claim 15, characterized in that the pressure above atmospheric and the bottom operating temperature of the said first fractionating column are comprised between about $15 \times 10^5$ and $25 \times 10^5$ Pa, and between about $-15°$ C. and $+3°$ C., respectively, and in that the pressure above atmospheric and the head operating temperature of the said second fractionating column are comprised between about $28 \times 10^5$ Pa and between about $-13°$ C. and $+5°$ C., respectively, whereas the flow rate of the liquid fraction feed to the said second fractionating column is equal to about 25% to 75%, preferably to about 40% to 50% of the flow rate of the liquid condensate D fed to the first fractionating column, the weight concentration of ethylene in the said liquid fraction being comprised between about 85% and 35%, preferably between about 35% and 45%.

20. A method according to claim 15, wherein said apparatus is characterized in that the withdrawing point is located in the region of the first bottom tray of the first fractionating column.

21. A method according to claim 20, characterized in that the pressure above atmospheric and the operating temperature at the bottom of the said first fractionating column are comprised between about $15 \times 10^5$ Pa and $25 \times 10^5$ Pa, and between about $-30°$ C. and $+3°$ C., respectively, and in that the pressure above atmospheric and the operating temperature at the head of the said second fractionating column are comprised between about $20 \times 10^5$ Pa and $45 \times 10^5$ Pa and between about $-28°$ C. and $+5°$ C., respectively, whereas the flow rate of the liquid fraction feed L to the second fractionating column is equal to about 25% to 75%, preferably about 40% to 50% of the flow rate of the condensate feed D to the first fractionating column, the weight concentration of ethylene in the said liquid fraction L being comprised between about 85% and 30%, preferably between about 70% and 35%.

22. A method according to claim 20, wherein said apparatus is characterized by a first heat exchanger, one of the circuits of which is connected to the feed duct to the second fractionating column, whereas the other circuit is connected either to the bottom of the said second fractionating column or to the bottom of the said first fractionating column.

23. A method according to claim 20, wherein said apparatus is characterized by a second heat exchanger, one of the circuits of which is connected to the head of the first fractionating column, whereas the other circuit is connected to the bottom of the said first fractionating column and/or to the bottom of the second fractionating column.

24. A method according to claim 20, wherein said apparatus is characterized by a third heat exchanger, one of the circuits of which is connected to the gas withdrawing duct from the head of the said first fractionating column, whereas the other circuit is connected to the bottom of the first fractionating column and/or to the bottom of the second fractionating column and, preferably, downstream of the first and second heat exchangers, if any.

* * * * *